US010202580B2

(12) United States Patent
Suematsu et al.

(10) Patent No.: US 10,202,580 B2
(45) Date of Patent: Feb. 12, 2019

(54) ADULT OLIGODENDROCYTE-TYPE 2 ASTROCYTE PROGENITOR CELL PRODUCTION METHOD

(71) Applicant: Japan Science and Technology Agency, Kawaguchi-shi, Saitama (JP)

(72) Inventors: Makoto Suematsu, Tokyo (JP); Yasuhito Tokumoto, Tokyo (JP); Shinpei Tamaki, Tokyo (JP)

(73) Assignee: JAPAN SCIENCE AND TECHNOLOGY AGENCY, Kawaguchi-Shi (JP)

( * ) Notice: Subject to any disclaimer, the term of this patent is extended or adjusted under 35 U.S.C. 154(b) by 29 days.

(21) Appl. No.: 15/112,027

(22) PCT Filed: Jan. 21, 2015

(86) PCT No.: PCT/JP2015/051485
§ 371 (c)(1),
(2) Date: Nov. 18, 2016

(87) PCT Pub. No.: WO2015/111602
PCT Pub. Date: Jul. 30, 2015

(65) Prior Publication Data
US 2017/0067020 A1 Mar. 9, 2017

(30) Foreign Application Priority Data
Jan. 21, 2014 (JP) ................. 2014-008780

(51) Int. Cl.
*C12N 5/0797* (2010.01)
*A61K 35/30* (2015.01)
*G01N 33/50* (2006.01)

(52) U.S. Cl.
CPC ............ *C12N 5/0623* (2013.01); *A61K 35/30* (2013.01); *G01N 33/5058* (2013.01); *C12N 2500/02* (2013.01); *C12N 2500/38* (2013.01); *C12N 2501/385* (2013.01); *C12N 2501/395* (2013.01)

(58) Field of Classification Search
None
See application file for complete search history.

(56) References Cited

U.S. PATENT DOCUMENTS

2007/0264712 A1* 11/2007 Savant-Bhonsale ........................
C12N 5/0623
435/377

FOREIGN PATENT DOCUMENTS

| JP | 2010-158242 A | 7/2010 |
| WO | 2003/000868 A1 | 1/2003 |
| WO | 2012/095730 A1 | 7/2012 |
| WO | 2013/021381 A1 | 2/2013 |

OTHER PUBLICATIONS

Engel et al. "Oligodendrocyte-type-2 astrocyte (O-2A) progenitor cells derived from adult rat spinal cord: in vitro characteristics and response to PDGF, bFGF and NT-3." Glia 16(1): 16-26, 1996 (Year: 1996).*
Guus Wolswijk et al., "Coexistence of perinatal and adult forms of a glial progenitor cell during development of the rat optic nerve," Development, vol. 109, pp. 691-698 (1990).
Dean G. Tang et al., "Long-Term Culture of Purified Postnatal Oligodendrocyte Precursor Cells: Evidence for an Intrinsic Maturation Program that Plays out over Months," The Journal of Cell Biology, vol. 148, No. 5, pp. 971-984 (2000).
Yasuhito M. Tokumoto et al., "Two molecularly distinct intracellular pathways to oligodendrocyte differentiation: role of a p53 family protein," The EMBO Journal, vol. 20, No. 18, pp. 5261-5268 (2001).
S. Kitamoto et al., "MUC1 enhances hypoxia-driven angiogenesis through the regulation of multiple proangiogenic factors," Oncogene, vol. 32, pp. 4614-4621 (2013).
Yoshimi Sekiguchi et al., "Rapamycin inhibits transforming growth factor β-induced peritoneal angiogenesis by blocking the secondary hypoxic response," Journal of Cellular and Molecular Medicine, vol. 16, No. 8, pp. 1934-1945 (2012).
Jared W. Allen et al., "In Vitro Liver Tissue Model Established from Transgenic Mice: Role of HIF-1alpha on Hypoxic Gene Expression," Tissue Engineering, vol. 12, No. 11, pp. 3135-3147 (2006).
B. A. Barres et al., "Cell Death and Control of cell Survival in the Oligodendrocyte Lineage," Cell, vol. 70, pp. 31-46 (Jul. 10, 1992).
S. Y. Christin Chong and Jonah R. Chan, "Tapping into the glial reservoir: cells committed to remaining uncommitted," The Journal of Cell Biology, vol. 188, No. 3, pp. 305-312 (2010).
Veronique E. Miron et al., "Cells of the oligodendroglial lineage, myelination, and remyelination," Biochimica et Biophysica Acta, vol. 1812, Issue 2, pp. 184-193 (2011).
Jeffrey K. Huang and Robin J.M. Franklin, "Current status of myelin replacement therapies in multiple sclerosis," Progress in Brain Research, vol. 201, Chapter 12, pp. 219-231 (2012).
Tamir Ben-Hur et al., "Growth and Fate of PSA-NCAM+ Precursors of the Postnatal Brain," The Journal of Neuroscience, vol. 18 (15), pp. 5777-5788 (Aug. 1, 1998).
Nathalie Gago et al., "Control of cell survival and proliferation of postnatal PSA-NCAM+ progenitors," Molecular and Cellular Neuroscience, vol. 22, Issue 2, pp. 162-178 (Feb. 2003).

(Continued)

*Primary Examiner* — Emily A Cordas (57) ABSTRACT

The present invention provides a method for producing adult oligodendrocyte progenitor cells from proliferative oligodendrocyte progenitor cells, and a pharmaceutical composition having for an active ingredient thereof adult OPC produced according to that method. The method for producing adult OPC of the present invention is characterized by inducing proliferating OPC to differentiate into adult OPC by culturing in the presence of a ligand of a thyroid hormone receptor or retinoic acid receptor in a low oxygen environment. The present invention further provides adult OPC produced according to the production method of the present invention, and a pharmaceutical composition having these adult OPC as an active ingredient thereof.

5 Claims, 6 Drawing Sheets

(56) References Cited

OTHER PUBLICATIONS

Oliver Bögler et al., "Cooperation between two growth factors promotes extended self-renewal and inhibits differentiation of oligodendrocyte-type-2 astrocyte (O-2A) progenitor cells," Proceedings of the National Academy of Sciences, vol. 87, No. 16, pp. 6368-6372 (Aug. 1990).
Kaylene M. Young et al., "Oligodendrocyte Dynamics in the Healthy Adult CNS: Evidence for Myelin Remodeling," Neuron, vol. 77, Issue 5, pp. 873-885 (Mar. 6, 2013).
Dean G. Tang et al., "Lack of Replicative Senescence in Cultured Rat Oligodendrocyte Precursor Cells," Science, vol. 291, pp. 868-871 (Feb. 2, 2001).
International Search Report received for PCT Patent Application No. PCT/JP2015/051485 dated Apr. 14, 2015, 4 pages (2 pages of English Translation of International Search Report, 2 pages of International Search Report).
B. A. Barres et al., "A novel role for thyroid hormone, glucocorticoids and retinoic acid in timing oligodendrocyte development," Development, 120, pp. 1097-1108 (1994).
Charles ffrench-Constant and Martin C. Raff, "Proliferating bipotential glial progenitor cells in adult rat optic nerve," Nature, vol. 319, pp. 499-502 (Feb. 6, 1986), Nature Publishing Group.
Jingyi Shi et al., "Purification and Characterization of Adult Oligodendrocyte Precursor Cells from the Rat Optic Nerve," The Journal of Neuroscience, 18 (12), pp. 4627-4636 (Jun. 15, 1998), the Society for Neuroscience.

\* cited by examiner

FIG. 10

ADULT OLIGODENDROCYTE-TYPE 2 ASTROCYTE PROGENITOR CELL PRODUCTION METHOD

CROSS REFERENCE TO RELATED APPLICATIONS

This application is a U.S. national stage application under 35 U.S.C. § 371 of International Patent Application No. PCT/JP2015/051485 filed on Jan. 21, 2015, which claims the benefit of foreign priority to Japanese Patent Application No. JP 2014-008780 filed on Jan. 21, 2014. The International Application was published in Japanese on Jul. 30, 2015, as International Publication No. WO 2015/111602 A1 under PCT Article 21(2).

TECHNICAL FIELD

The present invention relates to a method for producing oligodendrocyte-type 2 astrocyte progenitor cells observed in adults that remain dormant while retaining the ability to differentiate (to also be referred to as "adult OPC") from oligodendrocyte-type 2 astrocyte progenitor cells that actively undergo repeated cell division observed in organogenesis and soon after birth (to also be referred to as "proliferating OPC").

BACKGROUND ART

Oligodendrocytes are a type of glial cell found in the central nervous system that are formed by maturation of oligodendrocyte-type 2 astrocyte (O-2A) progenitor cells (abbreviated as OPC in the present application), and are mainly responsible for the formation of myelin sheath. OPC are the products of further differentiation of glial progenitor cells that have differentiated from neural stem cells. Although OPC actively undergo repeated cell division during organogenesis, a portion of those cells mature soon after birth and begin to differentiate into oligodendrocytes, and in adults, differentiate into oligodendrocytes, with the exception of some cells (adult OPC). Adult OPC observed in adults differ from proliferating OPC observed during organogenesis and soon after birth in that they are in a dormant state without hardly any proliferation. However, adult OPC retain the ability to differentiate and differentiate into oligodendrocytes in the presence of a suitable stimulus. In other words, adult OPC are a type of somatic stem cells.

Proliferating OPC harvested from the optic nerve of rats soon after birth have been reported to not differentiate into oligodendrocytes if cultured in serum-free media containing platelet-derived growth factor (PDGF) in an environment having an oxygen concentration of 20% by volume, but differentiate into oligodendrocytes when cultured in serum-free media containing PDGF and thyroid hormone, and proliferating OPC have been reported to be able to be sub-cultured in serum-free media containing PDGF over a long period of time of one year or longer while retaining the properties of proliferating OPC but without undergoing replicative senescence (see, for example, Non-Patent Document 2). In addition, retinoic acid has been reported to induce differentiation of OPC into oligodendrocytes in the same manner as thyroid hormone, and both have been reported to function mediated by the same p53-dependent intracellular signaling pathway (see, for example, Non-Patent Document 3).

PRIOR ART DOCUMENTS

Non-Patent Documents

Non-Patent Document 1: Wolswijk, et al., Development, 1990, Vol. 109, p. 691-698
Non-Patent Document 2: Tang, et al., The Journal of Cell Biology, 2000, Vol. 148(5), p. 971-984
Non-Patent Document 3: Tokumoto, et al., The EMBO Journal, 2001, Vol. 20(18), p. 5261-5268

DISCLOSURE OF THE INVENTION

Problems to be Solved by the Invention

On the other hand, although adult OPC are the result of induced differentiation of proliferating OPC (see, for example Non-Patent Document 1), the mechanism behind that induced differentiation remains unclear. A fairly large amount of adult OPC is required to conduct research on the physiological functions of adult OPC. In addition, adult OPC contribute to the formation of myelin sheath by differentiating into oligodendrocytes in the presence of a suitable stimulus. In other words, although myelin sheath can be repaired by the transmigration of adult OPC to a site of myelin sheath damage or demyelination, a fairly large amount of adult OPC are required for use as a cell therapeutic agent. However, in addition to only being present in trace amounts in the adult central nervous system, since they exhibit hardly any proliferation, it has been extremely difficult to prepare sufficient amounts of adult OPC.

A main object of the present invention is to provide a method for producing adult OPC, which had previously been difficult to acquire in large amounts, from proliferating OPC that are comparatively readily available, and a pharmaceutical composition having as an active ingredient thereof adult OPC produced according to this method.

Means for Solving the Problems

As a result of conducting extensive research, the inventors of the present invention found that, by stimulating with a ligand of a thyroid hormone receptor or retinoic acid receptor in a low oxygen environment, proliferating OPC are induced to differentiate into adult OPC that hardly proliferate at all despite retaining the ability to differentiate, thereby leading to completion of the present invention.

Namely, a method for producing adult OPC, adult OPC, a pharmaceutical composition, and a method for screening for substances having the ability to induce differentiation of adult OPC according to the present invention have the configurations indicated in [1] to [9] below.

[1] A method for producing adult OPC, comprising: a step for inducing proliferating OPC to differentiate into adult OPC by culturing in the presence of a ligand of a thyroid hormone receptor or retinoic acid receptor in a low oxygen environment.

[2] The method for producing adult OPC of [1] above, wherein the ligand is thyroid hormone, retinoic acid or vitamin A.

[3] The method for producing adult OPC of [1] or [2] above, wherein an oxygen concentration of the low oxygen environment is 0.5% by volume to 1.5% by volume.

[4] The method for producing adult OPC of [3] above, wherein the oxygen concentration is 0.5% by volume to 1.0% by volume.

[5] The method for producing adult OPC of any of [1] to [4] above, wherein the proliferative oligodendrocyte progenitor cells are cells obtained by primary culturing or sub-culturing proliferating OPC harvested from a living body.

[6] Adult OPC produced by the method for producing adult OPC of any of [1] to [5] above.

[7] A pharmaceutical composition comprising, as an active ingredient thereof, the adult OPC of [6] above.

[8] The pharmaceutical composition of [7] above, which is for treatment of hypomyelination, demyelination, or myelin sheath damage.

[9] A method for screening for substances having an ability to induce proliferation or induce differentiation of adult OPC, comprising:

a culturing step for culturing the adult OPC of [6] above in a medium containing a candidate substance for the ability to induce proliferation or induce differentiation, a detection step for detecting proliferation of the adult OPC or cells induced to differentiate from the adult OPC and a step for evaluating that the candidate substance has the ability to induce proliferation or differentiation in adult OPC in the case, in the detection step, the adult OPC proliferate significantly or cells are detected that have been induced to differentiate from the adult OPC.

Effects of the Invention

According to the present invention, adult OPC in a dormant state despite retaining the ability to induce differentiation can be efficiently produced from proliferating OPC that actively undergo repeated differentiation simply by regulating culturing conditions. In particular, by applying the method for producing adult OPC according to the present invention to proliferating OPC that have been preliminarily allowed to proliferate to an adequate amount, comparatively homogeneous adult OPC can be obtained in a sufficient amount. In addition, the resulting adult OPC are effective for not only scientific research, but also as a cell therapeutic agent.

BEST MODE FOR CARRYING OUT THE INVENTION

The method for producing adult OPC according to the present invention (to also be referred to as the "adult OPC production method according to the present invention") is characterized by having a step for inducing proliferating OPC to differentiate into adult OPC by culturing in the presence of a ligand of a thyroid hormone receptor or retinoic acid receptor in a low oxygen environment. As is disclosed in Non-Patent Document 2 and Non-Patent Document 3, thyroid hormone and retinoic acid are known to be factors that induce differentiation from OPC to oligodendrocytes in an environment having an oxygen concentration of 20% by volume. These factors were found for the first time by the inventors of the present invention to not function as differentiation induction factors in a low oxygen environment, but rather function as factors that induce differentiation to adult OPC in a dormant state, or in other words, induce proliferating OPC to differentiate into adult OPC by stimulating with a thyroid hormone receptor or retinoic acid receptor together with a hypoxic stimulus.

The proliferating OPC used in the adult OPC production method according to the present invention are OPC that actively undergo repeated cell division observed during organogenesis and soon after birth, and refer to cells having a cell cycle of 50 hours or less. The proliferating OPC used in the present invention may be proliferating OPC per se harvested from a living organism during organogenesis or soon after birth, or may be cells that have been allowed to proliferate by primary culturing or sub-culturing of proliferating OPC harvested from a living body. In addition, proliferating OPC differentiated from embryonic stem (ES) cells or induced pluripotent stem (iPS) cells can also be used in the present invention.

Harvesting of proliferating OPC from a living body and the subsequent culturing thereof can be carried out in accordance with ordinary methods. Proliferating OPC can be harvested in large numbers from the optic nerve in particular. For example, proliferating OPC can be harvested by excising the optic nerve of a rat soon after birth (1 to 10 days after birth) and slicing into sections, preparing a single cell suspension from the resulting sections, and isolating proliferating OPC from the single cell suspension by an immunological technique using antibody such as A2B5 antibody that recognizes molecules specifically expressed on the surface of proliferating OPC. There are no particular limitations on the medium used to culture the isolated proliferating OPC provided it is a medium that allows the proliferating OPC to be cultured without inducing differentiation. For example, proliferating OPC can be cultured in serum-free modified B-S medium or serum-free DMEM medium. At that time, an additive such as insulin, forskolin, PDGF-AA or neurotrophin-3 (NT-3) is preferably added to the medium. Proliferating OPC can be allowed to proliferate particularly efficiently by stimulating with PDGF-AA. Culturing at this time may be carried out at a standard oxygen concentration (roughly 20% by volume), may be carried out at the oxygen concentration in a living body (equivalent to an oxygen concentration of about 0.5% by volume to 8% by volume in the brain, although varying according to the particular tissue), or may be carried out at a low oxygen concentration (1.5% by volume or less).

In the adult OPC production method according to the present invention, the oxygen concentration of the gas used during culturing in order to induce differentiation of proliferating OPC into adult OPC is a concentration that is low enough to allow hypoxic stimulation of the proliferating OPC used. The upper limit value of oxygen concentration able to impart a hypoxic stimulus varies somewhat according to the tissue and species serving as the origin of those cells. The upper limit value of oxygen concentration that imparts a hypoxic stimulus to the proliferating OPC used can be determined experimentally as shown, for example, in Example 6 to be subsequently described. In the present invention, the oxygen concentration when culturing proliferating OPC in order to induce differentiation into adult OPC is preferably that of an environment having an oxygen concentration of 1.5% by volume or less, more preferably an environment having an oxygen concentration of 0.5% by volume to 1.5% by volume, even more preferably an environment having an oxygen concentration of 0.5% by volume to 1.2% by volume, and still more preferably an environment having an oxygen concentration of 0.5% by volume to 1.0% by volume. As described in a report by Kitamoto, et al. (Kitamoto, et al., Oncogene, 2013, Vol. 32, p. 4614-4621), a report by Sekiguchi, et al. (Sekiguchi, et al., Journal of Cellular and Molecular Medicine, 2012, Vol. 16(8), p. 1934-1045), and a report by Allen, et al. (Allen, et al., Tissue Engineering, 2006, Vol. 12(11), p. 3135-3147), hypoxic stimuli can be imparted to cells derived from various species of living organisms such as humans, rats or mice by adjusting oxygen concentration to 1% by volume or less.

In the adult OPC production method according to the present invention, although there are no particular limitations on the gas composition other than the oxygen concentration of the gas during culturing in order to induce proliferating OPC to differentiate into adult OPC, the main component of the gas other than oxygen is preferably nitrogen, and the gas may also contain carbon dioxide. In the case of containing carbon dioxide, carbon dioxide concentration is preferably about 3% by volume to 10% by volume.

In the adult OPC production method according to the present invention, proliferating OPC are specifically cultured in a medium to which has been added a ligand of a thyroid hormone receptor or retinoic acid receptor in a gas having a low oxygen concentration. Examples of such media include medium obtained by adding a ligand of a thyroid hormone receptor or retinoic acid receptor to a medium such as serum-free modified B-S medium or serum-free DMEM medium that allows proliferating OPC to proliferate without inducing differentiation.

Examples of ligands of thyroid hormone receptors used in the present invention include 3,5,3',5'-tetraiodo-L-thyronine (T4, also referred to as thyroxine) and 3,5,3'-triiodo-L-thyronine (T3). In addition, tetrazole compounds that have a structure that resembles T3 or T4 and are capable of binding with thyroid hormone receptors may also be used. Examples of ligands of retinoic acid receptors used in the present invention include retinoic acid and vitamin A. The ligand used in the present invention is preferably T4, T3 or all-trans retinoic acid.

Proliferating OPC cells may be cultured in medium containing only one type of ligand or may be cultured in medium containing two or more types of ligands. In addition, the medium may contain both a ligand of a thyroid hormone receptor and a ligand of a retinoic acid receptor. More specifically, the medium may be a medium that contains one of either T3 or T4, a medium that contains both T3 and T4, or a medium that contains at least one of T3 and T4 and retinoic acid.

Although adult OPC obtained according to the adult OPC production method according to the present invention are in a dormant state in which proliferation has ceased, they retain pluripotency and the ability to re-proliferate. Consequently, the resulting adult OPC are induced to undergo re-division and differentiation by a suitable stimulus in the same manner as adult OPC present in a living body. For example, the adult OPC undergo re-division as a result of being stimulated with PDGF, neuregulin (NRG) and a phosphodiesterase 1 inhibitor in the form of 1-methyl-3-(2-methylpropyl)xanthine (IBMX). On the other hand, these adult OPC differentiate to oligodendrocytes as a result of stimulating with PDGF and TH in an environment having an oxygen concentration of 20%.

According to the adult OPC production method according to the present invention, comparatively homogeneous adult OPC can be supplied more stably and in larger numbers than in the prior art. Consequently, the use of the resulting adult OPC as model cells and the like can be expected to dramatically accelerate the pace of research on the functions of adult OPC.

Myelin sheath can be expected to be repaired by the transmigration of adult OPC to sites of myelin sheath damage, demyelination sites or hypomyelination sites. In addition, differing from proliferating OPC, since adult OPC are in a dormant state while retaining the ability to differentiate, they offer the advantage of a lower risk of malignant transformation.

Consequently, adult OPC obtained according to the adult OPC production method according to the present invention can be used as an active ingredient of a pharmaceutical composition. This pharmaceutical composition is preferably used to treat hypomyelination, demyelination or myelin sheath damage. More specifically, these adult OPC can be expected to serve as active ingredients of pharmaceutical compositions used to treat and prevent, for example, trauma, amyotrophic lateral sclerosis (ALS), Parkinson's disease, multiple sclerosis (MS), progressive multifocal leukoencephalopathy (PML), encephalomyelitis (EPL), central pontine myelinolysis (CPM), Wallerian degeneration, adrenoleukodystrophy, Alexander disease, Pelizaeus-Merzbacher disease (PMD) or macular hole.

The adult OPC obtained according to the adult OPC production method according to the present invention can also be used to screen for substances having the ability to induce proliferation or induce differentiation of adult OPC. For example, screening of candidate substances can be carried out by carrying out a detection step, in which adult OPC are cultured in a medium containing the candidate substance for the ability to induce proliferation or induce differentiation, and measuring whether or not the adult OPC undergo re-division, or in other words, whether or not the number of adult OPC in the medium is increased by culturing, or detecting whether the adult OPC differentiate into oligodendrocytes, or in other words, whether antigen specific to differentiated cells is expressed in cells in the medium; and then respectively evaluating the candidate substance as having the ability to induce proliferation or induce differentiation in the adult OPC in the case the adult OPC have proliferated significantly or in the case cells are detected that have been induced to differentiate from the adult OPC. Confirmation of a difference in uptake of bromodeoxyuridine (BrdU) or confirmation of expression of a proliferation marker in the form of Ki-67 protein can be used as means for confirming the ability to induce proliferation. In the case the adult OPC undergoes re-division and the number of adult OPC increases significantly in the medium (two-fold or more and preferably ten-fold or more), the candidate substance added to the medium can be evaluated as having the ability to induce proliferation of adult OPC. In addition, in the case the adult OPC have differentiated into oligodendrocytes and antigen specific to differentiated cells is detected in cells in the medium, the candidate substance added to the medium can be evaluated as having the ability to induce differentiation of adult OPC. Examples of antigens specific to differentiated cells include galactocerebroside (GC), proteolipid protein (PLP), 2',3'-cyclic-nucleotide 3'-phosphodiesterase (CNPase) and myelin basic protein (MBP).

EXAMPLES

Although the following provides a more detailed explanation of the present invention through examples thereof, the present invention is not limited by these examples. In addition, all of the animal experiment protocols indicated below were approved by the ethics committee of Keio University.

In addition, unless specifically indicated otherwise, the proliferating OPC used in the following examples were isolated from the optic nerves of 7-day-old rats (P7) in accordance with the immunopanning method of Barres, et al. (Barres, et al., Cell, 1992, Vol. 70, p. 31-46), and the purity thereof (percentage of proliferating OPC relative to all cells) was 99.9% or more.

Example 1

Proliferating OPC were cultured in medium containing thyroid hormone or medium not containing thyroid hormone in an environment having an oxygen concentration of 1.5% by volume followed by investigating the effect of thyroid hormone on the proliferation ability of the proliferating OPC.

1000 proliferating OPC per flask were seeded into T25 culture flasks coated with poly-D-lysine (PDL) followed by culturing for 15 days each at 37° C. in a gas having an oxygen concentration of 1.5% by volume and carbon dioxide concentration of 5% by volume in TH-containing medium to which was added a thyroid hormone mixture (mixture consisting of equal parts of T3 and T4 (40 ng/mL), abbreviated as "TH") or TH-free medium not containing TH. Serum-free modified B-S medium to which was added PDGF-AA (10 ng/mL), NT-3 (5 ng/mL), insulin (5 μg/mL) and forskolin (5 μM) was used for the TH-free medium, while medium obtained by adding TH (T3 and T4: 40 ng/mL each) to TH-free medium was used for the TH-containing medium.

Figure 1:
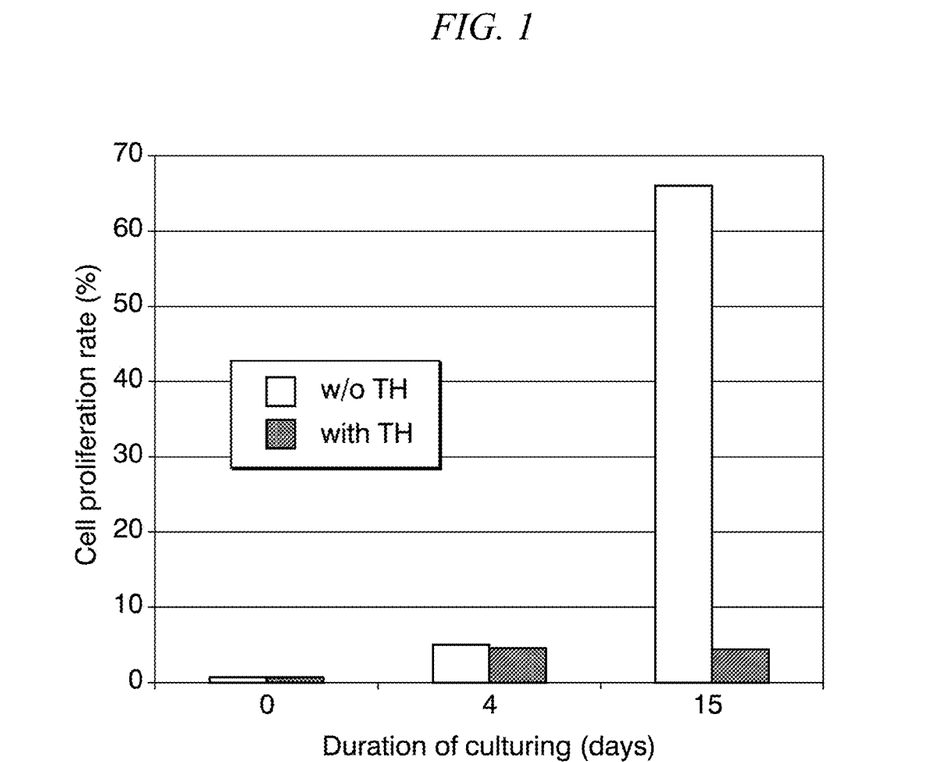
FIG. 1 is a graph showing the results of calculating cell proliferation rates (multiples) in the case of having cultured proliferating OPC in thyroid hormone (TH)-containing medium and in the case of culturing in TH-free medium in Example 1.

The results of counting the numbers of cells in each flask are shown in Table 1, while the results of calculating the cell proliferation rates (multiples) are shown in FIG. 1. In the TH-free medium, the number of cells increased to more than 60 times the initial number of cells on day 15 ("Absence of thyroid hormone" in Table 1, "w/o TH" in FIG. 1). On the other hand, in the TH-containing medium, although proliferation similar to that of the TH-free medium was observed through day 4 of culturing, the number of cells remained nearly constant thereafter and the cells ceased to proliferate ("Presence of thyroid hormone" in Table 1, "with TH" in FIG. 1). On the basis of these results, cells were confirmed to proliferate up to a certain time and subsequently cease to proliferate as a result of stimulating with TH in a low oxygen environment.

TABLE 1

| Duration of culturing (days) | Number of Cells | |
|---|---|---|
| | Absence of thyroid hormone | Presence of thyroid hormone |
| 0 | 1,000 | 1,000 |
| 4 | 50,000 | 45,000 |
| 15 | 660,000 | 44,000 |

Example 2

Proliferating OPC were cultured in medium to which was added thyroid hormone in an environment having an oxygen concentration of 1.5% by volume or 20% by volume followed by investigating the effect of thyroid hormone on the differentiation ability of the proliferating OPC.

300 proliferating OPC per culture dish were seeded into glass bottom culture dishes having a diameter of 12 mm and coated with PDL to prepare six culture dishes followed by culturing for 12 days at 37° C. in the TH-containing medium used in Example 1. Among the six culture dishes, three were cultured in a gas having an oxygen concentration of 1.5% by volume and carbon dioxide concentration of 5% by volume, while the remaining three culture dishes were cultured in a gas having an oxygen concentration of 20% by volume and carbon dioxide concentration of 5% by volume.

Following completion of culturing, the cells in each culture dish were fixed by treating for 5 minutes at room temperature in a 2.0% paraformaldehyde solution. Following primary immunostaining of the fixed cells using mouse anti-galactocerebroside (GC) antibody (provided by Martin C. Raff) and mouse A2B5 antibody (provided by Martin C. Raff), the cells were subjected to secondary staining with AlexaFluor™ 488-labeled mouse IgG antibody and AlexaFluor™ 568-labeled mouse IgM antibody (both available from Invitrogen Corp.) and then further stained with DAPI (Dojindo Laboratories Co., Ltd.). A2B5 antibody is an antibody that is specific for OPC, while GC is an oligodendrocyte marker.

Figure 2:
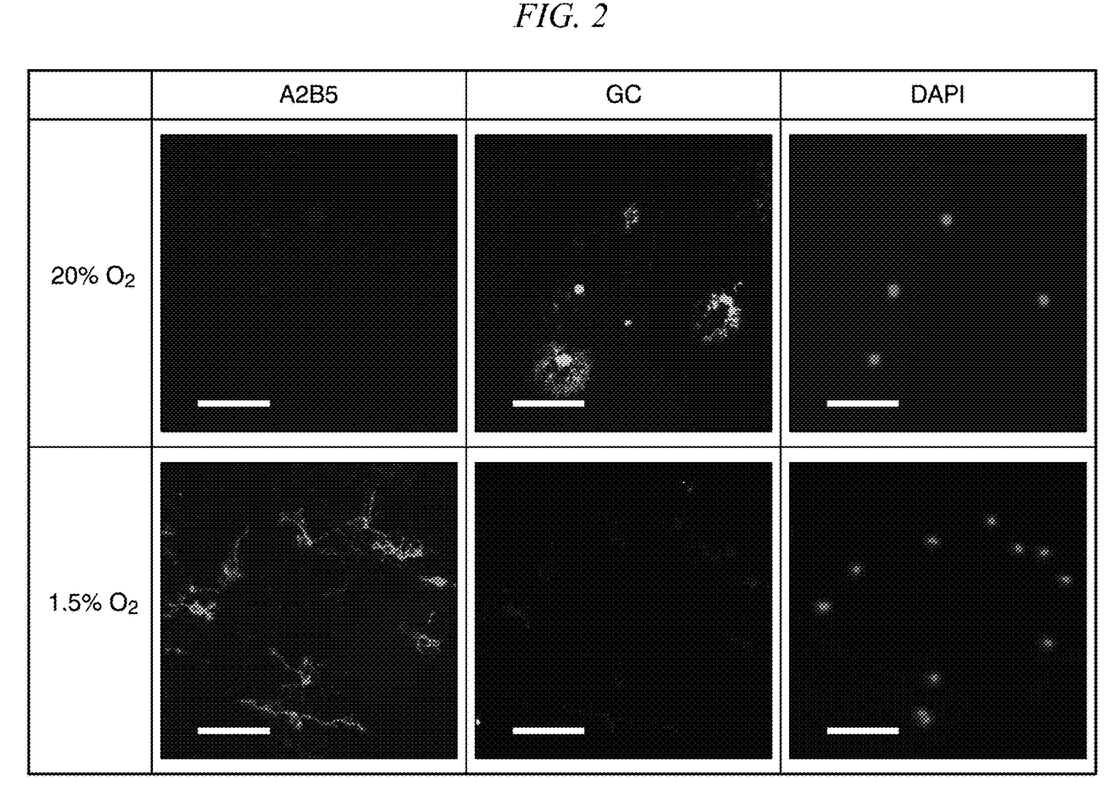
FIG. 2 shows stained images of cells cultured in TH-containing medium, in an environment having an oxygen concentration of 20% by volume (upper row) and in an environment having an oxygen concentration of 1.5% by volume (lower row), in Example 2.
Figure 3:
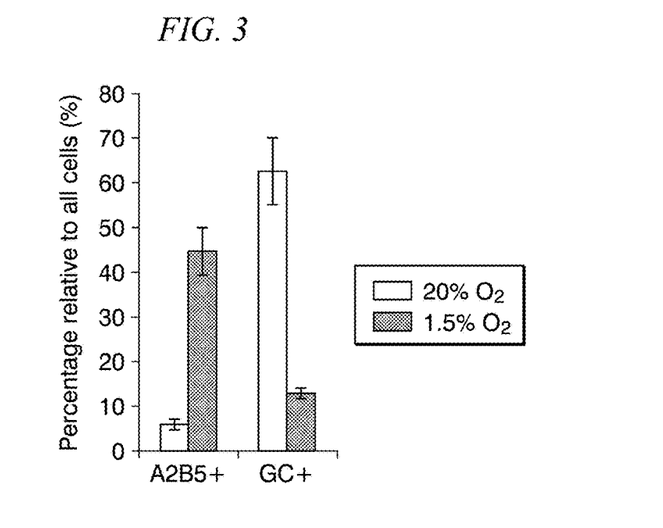
FIG. 3 is a graph showing the results of calculating the percentage of cells that were stained with anti-ganglioside GT3 antibody (A2B5 antibody) and the percentage of cells stained with anti-GC antibody, relative to all cells present in culture dishes, in Example 2.

FIG. 2 shows stained images of cells cultured in an environment having an oxygen concentration of 20% by volume (upper row) and stained images of cells cultured in an environment having an oxygen concentration of 1.5% by volume (lower row). In addition, FIG. 3 shows the results of calculating the percentage of cells that were stained with A2B5 antibody (A2B5-positive cells, "A2B5+" in the drawing) and the percentage of cells stained with anti-GC antibody (GC-positive cells, "GC+" in the drawing), relative to all cells present in the culture dishes. In FIG. 3, the bar on the left ("20% $O_2$") indicates the results for culturing in an environment having an oxygen concentration of 20% by volume, while the bar on the right ("1.5% $O_2$") indicates the results for culturing in an environment having an oxygen concentration of 1.5% by volume. As a result, roughly 65% of the cells cultured in an environment having an oxygen concentration of 20% by volume were GC-positive cells that had differentiated into oligodendrocytes. In contrast, only about 10% of the cells cultured in an environment having an oxygen concentration of 1.5% by volume were GC-positive cells, while roughly 45% were A2B5-positive OPC.

On the basis of the above, when considering together with the results of Example 1, in the case of having cultured proliferating OPC in medium containing thyroid hormone in an environment having a low oxygen concentration, although the cells proliferated until a certain time, proliferation subsequently ceased, thereby making it possible to confirm these cells to be adult OPC for which differentiation into oligodendrocytes had been inhibited.

Example 3

Proliferating OPC were cultured in medium to which was added thyroid hormone or medium to which was added retinoic acid in an environment having an oxygen concentration of 1.5% by volume followed by investigating the effect of retinoic acid (PA) on the proliferating OPC.

Six glass bottom culture dishes having a diameter of 12 mm and-coated with PDL were prepared by seeding with 300 proliferating OPC per culture disk, followed by culturing for 12 days at 37° C. in an environment having an oxygen concentration of 1.5% by volume and carbon dioxide concentration of 5% by volume. Three of the six culture dishes were cultured in the TH-containing medium used in Example 1, while the remaining three culture dishes were cultured in medium containing RA (medium obtained by adding all-trans retinoic acid (Sigma Corp., 1 ng/mL) to the TH-free medium used in Example 1).

Figure 4:
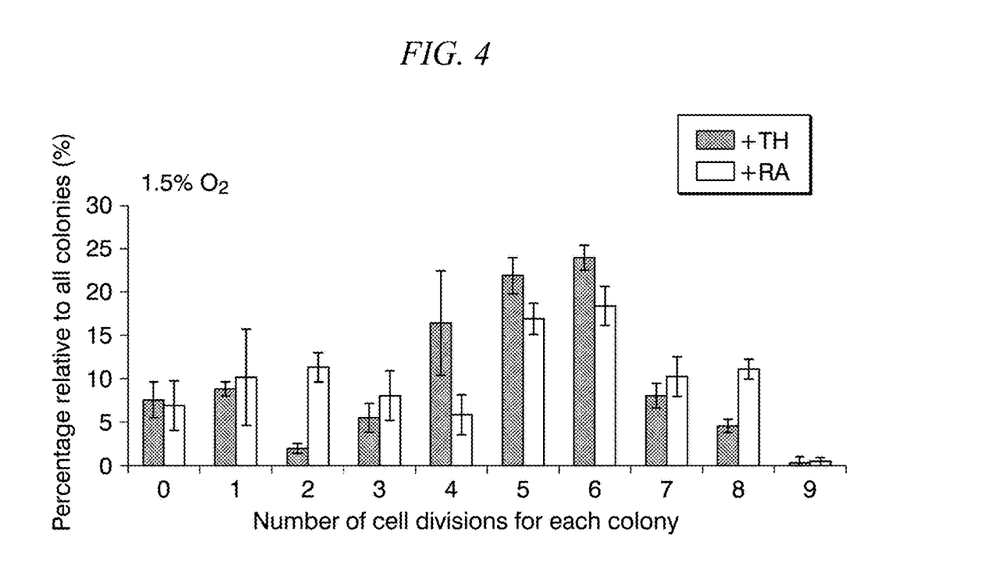
FIG. 4 is a graph showing the results of measuring the percentage (%) of all colonies having the respective number of cell divisions in the case of having cultured proliferating OPC in TH-containing medium or RA-containing medium in an environment having an oxygen concentration of 1.5% by volume, relative to all colonies, in Example 3.

Following completion of culturing, the numbers of cells that formed colonies were respectively counted and the number of cell divisions was determined for each colony. FIG. 4 shows the results of measuring the percentage (%) of colonies having the respective number of cell divisions, relative to all colonies. As a result, in the case of culturing in TH-containing medium ("+TH" in the drawing) and in the case of culturing in RA-containing medium ("+RA" in the drawing), the percentages of colonies having 5 to 6 cell divisions were the highest and there were no colonies for which the number of cell divisions exceeded 10.

Figure 5:
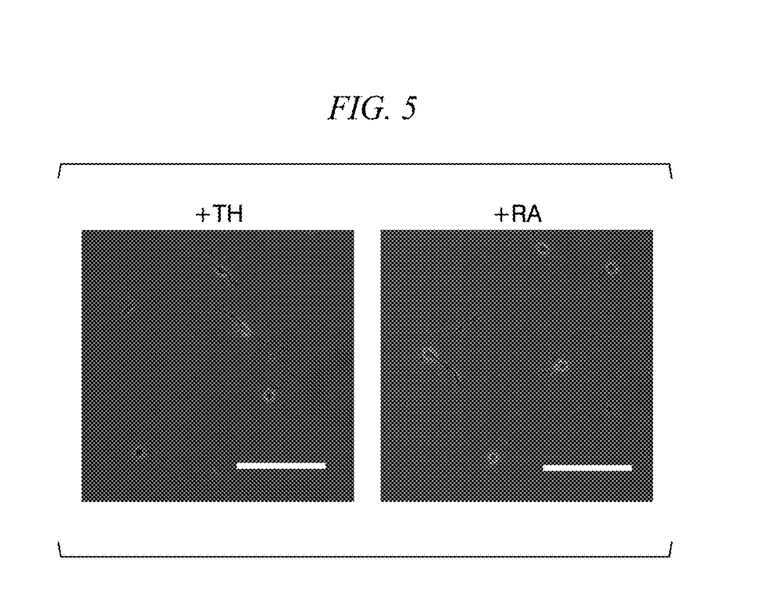
FIG. 5 shows phase-contrast micrographs of cells cultured in TH-containing medium (+TH) and cells cultured in RA-containing medium (+RA) in an environment having an oxygen concentration of 1.5% by volume, in Example 3.

In addition, FIG. 5 shows phase-contrast micrographs of cells cultured in TH-containing medium ("+TH") and cells cultured in RA-containing medium ("+RA"). Cells obtained after culturing proliferating OPC for 12 days in TH-containing medium and cells obtained after culturing proliferating OPC for 12 days in RA-containing medium exhibited similar morphology. On the basis of these results, retinoic acid was clearly determined to be able to interrupt proliferation of proliferating OPC and induce differentiation to adult OPC in a low oxygen environment in the same manner as thyroid hormone.

Example 4

An investigation was made as to whether or not adult OPC, obtained by hypoxic stimulation and TH-stimulation of proliferating OPC, have the ability to differentiate.

Six glass bottom culture dishes having a diameter of 12 mm and coated with PDL were prepared by seeding with 300 proliferating OPC per culture dish, followed by culturing for 15 days at 37° C. in the TH-containing medium used in Example 1 in an environment having an oxygen concentration of 1.5% by volume and carbon dioxide concentration of 5% by volume. Next, the medium of three of the six culture dishes were replaced with PDGF-free TH-containing medium (medium obtained by excluding PDGF from the TH-containing medium used in Example 1) followed by culturing for 5 days at 37° C. in gas having an oxygen concentration of 1.5% by volume and carbon dioxide concentration of 5% by volume. The medium of the remaining three culture dishes was replaced with FBS-containing medium (serum-free modified B-S medium containing FBS (10%)) followed by culturing for 5 days at 37° C. in a gas having an oxygen concentration of 1.5% by volume and carbon dioxide concentration of 5% by volume.

Following completion of culturing, the cells in each culture dish were fixed by treating for 5 minutes at room temperature with 2.0% formaldehyde solution followed by carrying out cell membrane permeation treatment. Following completion of cell membrane permeation treatment, the cells in one of the three culture dishes cultured with PDGF-free TH-containing medium and one of the three culture dishes cultured with FBS-containing medium were subjected to primary immunostaining using rat anti-MBP antibody (MAB386, Millipore Corp.) followed by subjecting to secondary staining using AlexaFluor™ 488-labeled mouse IgG antibody. Similarly, one of the three culture dishes cultured with PDGF-free TH-containing medium and one of the three culture dishes cultured with FBS-containing medium were subjected to primary immunostaining using mouse anti-CNPase antibody (C5922, Sigma Corp.) followed by subjecting to secondary staining using AlexaFluor™ 488-labeled mouse IgG antibody. After carrying out primary immunostaining on one of the three cultured dishes cultured with PDGF-free TH-containing medium and one of the three culture dishes cultured with FBS-containing medium using rabbit anti-GFAP antibody (G4546, Sigma Corp.), secondary staining was carried out using AlexaFluor™ 488-labeled anti-rabbit IgG antibody. 2',3'-cyclic-nucleotide 3'-phosphodiesterase (CNPase) and myelin basic protein (MBP) are oligodendrocyte markers, while glial fibrillary acidic protein (GFAP) is an astrocyte marker.

Figure 6:
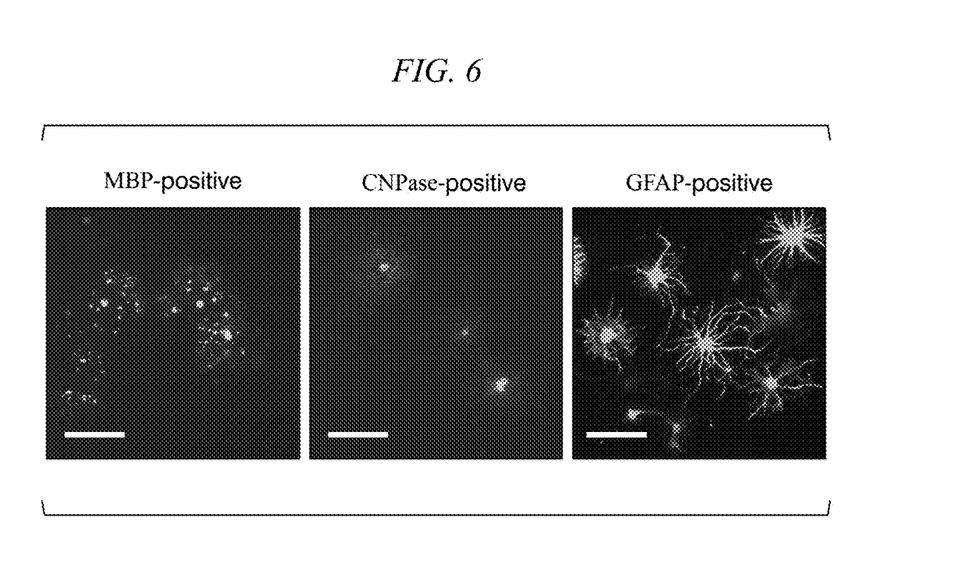
FIG. 6 shows stained images of MBP-positive cells and CNPase-positive cells present in culture dishes cultured in PDGF-free, TH-containing medium, and a stained image of GFAP-positive cells present in a culture dish cultured in FBS-containing medium, in Example 4.

FIG. 6 shows stained images of each of the cells. MBP-positive cells and CNPase-positive cells were present in the culture dish cultured with PDGF-free TH-containing medium ("MBP-positive" and "CNPase-positive" in the drawing). In contrast, GFAP-positive cells were present in the culture dish cultured with FBS-containing medium ("GFAP-positive" in the drawing). On the basis of these results, adult OPC obtained by subjecting proliferating OPC to hypoxic stimulation and TH stimulation were confirmed to be able to differentiate into oligodendrocytes and astrocytes in the presence of a suitable stimulus, namely these adult OPC were confirmed to retain the ability to differentiate in the same manner as proliferating OPC.

Example 5

An investigation was made of the ability of adult OPC, obtained by subjecting proliferating OPC to hypoxic stimulation and TH stimulation, to re-proliferate and differentiate.

1000 proliferating OPC per flask were seeded into T25 culture flasks coated with PDL followed by culturing in the TH-containing medium used in Example 1 for 15 days at 37° C. in a gas having an oxygen concentration of 1.5% by volume and carbon dioxide concentration of 5% by volume. Next, the cells were recovered from the culture flasks and three new T25 culture flasks coated with PDL were prepared by again seeding with 1000 recovered OPC per flask followed by culturing for 7 days at 37° C. in a gas having an oxygen concentration of 20% by volume and carbon dioxide concentration of 5% by volume. One of the three culture flasks was cultured with the TH-free medium used in Example 1, the remaining culture flask was cultured with the medium containing IN (medium obtained by adding NRG1 (50 ng/mL) and IBMX (0.1 mM) to the TH-free medium used in Example 1).

Figure 7:
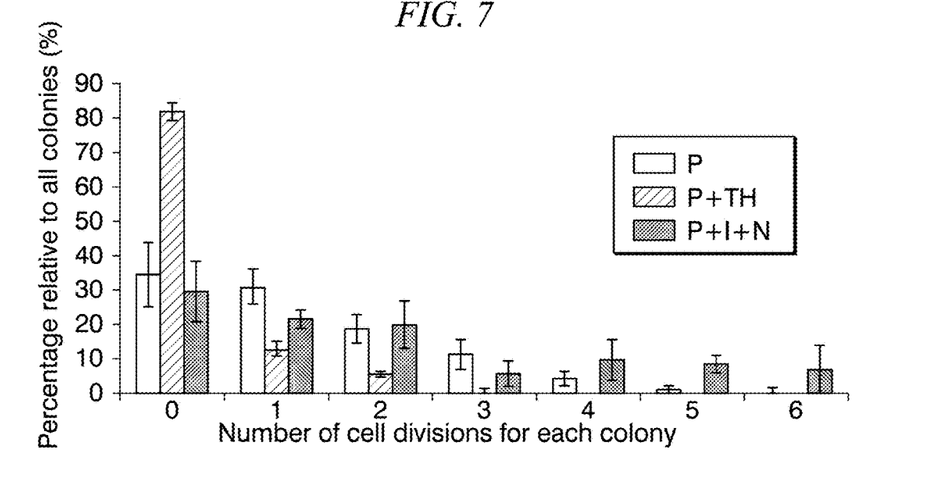
FIG. 7 is a graph showing the results of measuring the percentages (%) of colonies having the respective number of cell divisions in the case of having cultured adult OPC in various media in an environment having an oxygen concentration of 20% by volume, relative to all colonies, in Example 5.
Figure 8:
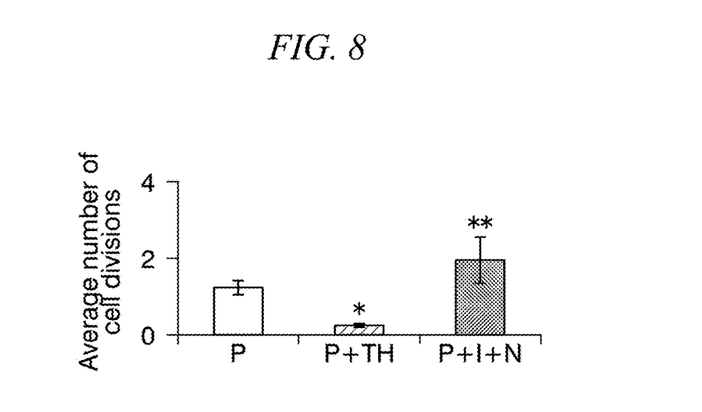
FIG. 8 is a graph showing the results of calculating the average number of cell divisions of colonies in the case of having cultured adult OPC in various media in an environment having an oxygen concentration of 20% by volume based on the results shown in FIG. 7, in Example 5.

Following completion of culturing, the numbers of cells that formed colonies were counted and the number of cell divisions was determined for each colony. FIG. 7 shows the results of measuring the percentage (%) of all colonies having the respective number of cell divisions, relative to all colonies. In addition, FIG. 8 shows the results of calculating the average number of cell divisions of colonies in the case of having cultured in each medium based on the results shown in FIG. 7. As a result, in the case of having cultured with the TH-free medium or IN-containing medium, nearly 70% of the colonies underwent cell division at least once, and although there were colonies that underwent cell division six times, cells that differentiated into oligodendrocytes were not observed ("P" and "P+I+N" in FIGS. 7 and 8). In contrast, in the case of culturing with TH-containing medium, the average number of cell divisions was less than 0.5 and cells were observed that had differentiated into oligodendrocytes ("P+TH" in FIGS. 7 and 8). On the basis of these results, adult OPC obtained by subjecting proliferating OPC to hypoxic stimulation and TH stimulation were confirmed to be able to re-proliferate as well as differentiate in the presence of a suitable stimulus.

Example 6

An investigation was made of the effect of oxygen concentration on proliferating OPC by culturing proliferating OPC in medium to which was added thyroid hormone in an environment having an oxygen concentration of 1.0, 1.5, 2.0, 2.5 or 3.0% by volume.

Five T25 culture flasks coated with PDL were prepared by seeding with 1000 proliferating OPC per flask, followed by culturing for 10 days at 37° C. in the TH-containing medium used in Example 1 in a gas having an oxygen concentration of 1.0% by volume to 3.0% by volume and having a carbon dioxide concentration of 5% by volume.

Figure 9:
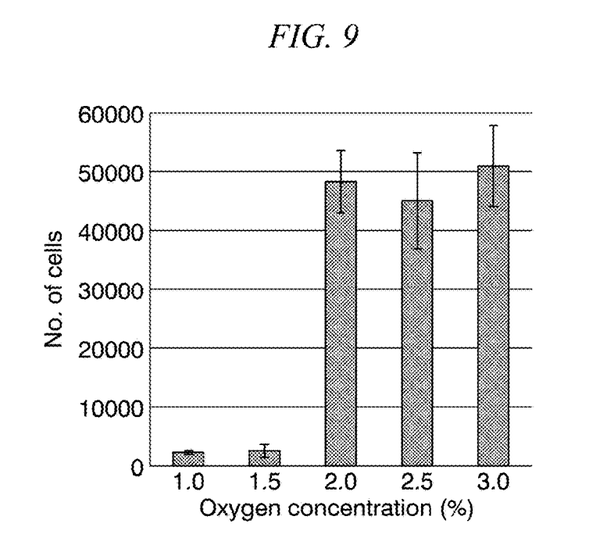
FIG. 9 is a graph showing the results of counting the numbers of viable cells in the case of having cultured in TH-containing medium in environments having various oxygen concentrations, in Example 6.

Following completion of culturing, the number of viable cells in each culture flask was counted. FIG. 9 shows the count results. As a result, in the case of having cultured in an environment having an oxygen concentration of 2.0, 2.5 or 3.0% by volume, the proliferating OPC proliferated to a viable cell count of 40,000 cells or more. In contrast, in the case of having cultured in an environment having an oxygen concentration of 1.0% by volume or 1.5% by volume, there were hardly any increases in the number of cells and proliferation was determined to have ceased. In other words, rat proliferating OPC cells were determined to have an upper limit (threshold value) between an oxygen concentration of 1.5% by volume and 2.0% by volume for the oxygen concentration capable of imparting a hypoxic stimulus.

Example 7

An investigation was made of the proliferation ability of proliferating OPC by culturing in medium to which was added thyroid hormone in an environment having an oxygen concentration of 1.0% by volume or 3.0% by volume using proliferating OPC having purity (percentage of proliferating OPC relative to all cells) of 99.9% or more isolated from the optic nerves of 7-day-old C57BL/6 mice in accordance with the immunopanning method of Barres, et al. (Barres, et al., Cell, 1992, Vol. 70, p. 31-46).

Six glass bottom culture dishes having a diameter of 12 mm and coated with PDL were prepared by seeding with 300 mouse proliferating OPC per flask, followed by culturing three of the culture dishes in a gas having an oxygen concentration of 1.0% by volume and carbon dioxide concentration of 5% by volume, and culturing the remaining three culture dishes in a gas having an oxygen concentration 3.0% by volume and carbon dioxide concentration of 5% by volume, for 12 days at 37° C. in the TH-containing medium used in Example 1, respectively.

Figure 10:
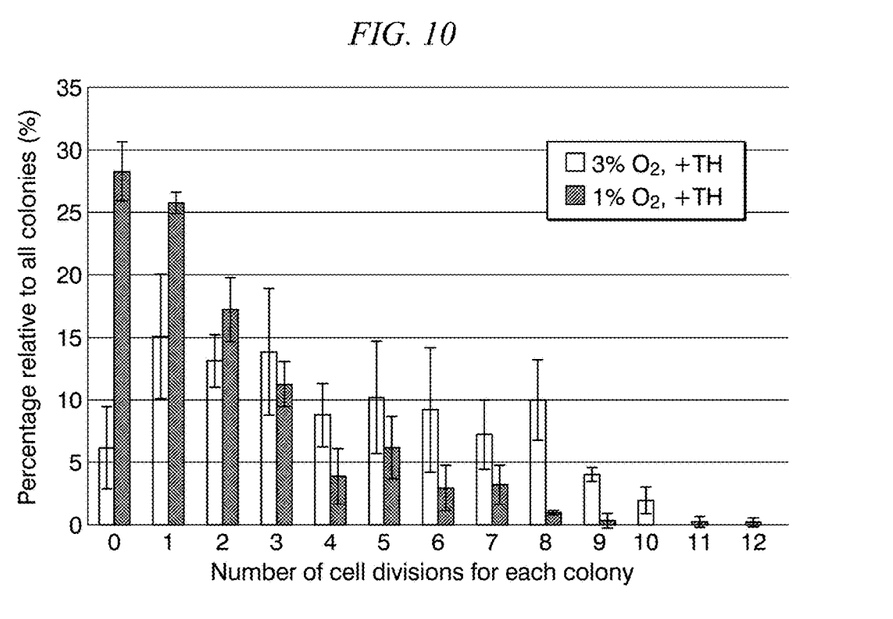
FIG. 10 is a graph showing the results of measuring the percentages (%) of all clones having the respective number of cell divisions in the case of having cultured mouse-derived proliferating OPC in TH-containing medium in an environment having an oxygen concentration of 1.0% by volume or 3.0% by volume, relative to all clones, in Example 7.

Following completion of culturing, the number of cells of each clone was counted and the respective numbers of cell divisions were estimated. More specifically, cells were estimated, for example, to undergo cell division three times in the case of 5 to 8 cells, and undergo cell division four times in the case of 9 to 16 cells. FIG. 10 shows the results of measuring the percentages (%) of clones having the respective number of cell divisions. As a result, in the case of cells cultured in an environment having an oxygen concentration of 3.0% by volume, clones having three or more cell divisions accounted for more than 50% of the clones, and cells were observed that underwent cell division 12 times. In contrast, in the case of cells cultured in an environment having an oxygen concentration of 1.0% by volume, nearly 70% of all clones underwent two or fewer cell divisions, about 27% of the clones did not undergo cell division even once, the number of cells hardly increased at all, and proliferation was determined to have ceased. On the basis of these results, mouse-derived proliferating OPC were also clearly determined to cease proliferation and be able to be induced to differentiate into adult OPC by subjecting to TH stimulation in an environment having an oxygen concentration of 1.0% by volume.

The invention claimed is:

1. A method for producing adult oligodendrocyte-type 2 astrocyte progenitor cells (adult OPC), comprising:
   proliferating oligodendrocyte-type 2 astrocyte progenitor cells (proliferating OPC) in a serum-free medium in the absence of a ligand of a thyroid hormone receptor or retinoic acid receptor; and
   inducing the proliferating OPC to differentiate into adult OPC by culturing in the presence of a ligand of a thyroid hormone receptor or retinoic acid receptor in a low oxygen environment,
wherein the ligand of a thyroid hormone receptor or retinoic acid receptor is selected from the group consisting of: 3,5,3',5'-tetraiodo-L-thyronine (T4), 3,5,3'-triiodo-L-thyronine (T3), a tetrazole compound having a structure similar to T4 or T3 and being able to bind to the thyroid hormone receptor; retinoic acid, and vitamin A.

2. The method for producing adult OPC according to claim 1, wherein the ligand is thyroid hormone, retinoic acid or vitamin A.

3. The method for producing adult OPC according to claim 1, wherein an oxygen concentration of the low oxygen environment is 0.5% by volume to 1.5% by volume.

4. The method for producing adult OPC according to claim 3, wherein the oxygen concentration is 0.5% by volume to 1.0% by volume.

5. The method for producing adult OPC according to claim 1, wherein the proliferating OPC are cells obtained by primary culturing or sub-culturing OPC harvested from a living body.

* * * * *